United States Patent [19]

Rudy et al.

[11] Patent Number: 4,837,008
[45] Date of Patent: Jun. 6, 1989

[54] PERIODONTAL COMPOSITION AND METHOD

[75] Inventors: Jerome B. Rudy; Melvin Denholtz, both of Livingston; Jeffrey R. Denholtz, Stanhope; Peter D. Bohm, Freehold, all of N.J.

[73] Assignee: Peroxydent Group, Livingston, N.J.

[21] Appl. No.: 2,177

[22] Filed: Jan. 12, 1987

Related U.S. Application Data

[63] Continuation-in-part of Ser. No. 721,210, Apr. 9, 1985, abandoned, which is a continuation-in-part of Ser. No. 532,182, Sep. 14, 1983, abandoned.

[51] Int. Cl.$^4$ .................. A61K 7/20; A61K 33/40
[52] U.S. Cl. .................................... 424/53; 424/613; 424/717
[58] Field of Search ................................ 424/53, 130

[56] References Cited

U.S. PATENT DOCUMENTS

| | | | |
|---|---|---|---|
| 959,605 | 5/1910 | Puelsser | 424/53 |
| 1,018,240 | 2/1912 | Von Foregger | 424/53 |
| 1,863,116 | 6/1932 | Heiman | 424/53 |
| 2,035,267 | 3/1936 | Fleischmann | 167/93 |
| 2,052,694 | 9/1936 | Breivogel | 167/93 |
| 2,054,742 | 9/1936 | Elbel | 167/93 |
| 2,090,437 | 8/1937 | Woldman | 167/93 |
| 2,218,172 | 10/1940 | Kokatnor | 167/93 |
| 3,671,629 | 6/1972 | Levy et al. | 424/153 |
| 4,487,757 | 12/1984 | Kiozpeoplou | 424/7.1 |
| 4,528,180 | 7/1985 | Schaeffer | 424/52 |
| 4,582,701 | 4/1986 | Piechota | 424/52 |
| 4,647,451 | 3/1987 | Piechota | 424/52 |
| 4,687,663 | 8/1987 | Schaeffer | 424/53 |
| 4,776,560 | 10/1988 | Ford | 424/53 |

OTHER PUBLICATIONS

PDR (1982), Non-Prescription Drugs, "Glyoxide", Marion Labs., p. 561.

*Primary Examiner*—Shep K. Rose
*Attorney, Agent, or Firm*—Klauber & Jackson

[57] ABSTRACT

A non-aqueous paste or gel dentifrice composition comprising a water soluble, non-aqueous vehicle having dispersed therein an orally acceptable organic or inorganic peroxide and a bicarbonate salt. The quantities and relative proportions of the peroxide and bicarbonate are sufficient to provide quantities of bactericidally active oxygen upon breakdown of said peroxide by tissue contact and/or by reaction with said bicarbonate in the oral cavity. The bicarbonate also provides a neutral or basic pH upon dissolution of the composition in water. The peroxide and/or bicarbonate is provided with a water soluble barrier coating which is insoluble in the vehicle, to prevent reaction therebetween in the absence of water dissolution of the coating. Normal dentifrice adjuvants may also be present, which can similarly be provided with a water soluble barrier coating.

27 Claims, No Drawings

PERIODONTAL COMPOSITION AND METHOD

RELATED APPLICATION

This application is a continuation-in-part of U.S. application Ser. No. 721,210, filed Apr. 9, 1985 abandoned, which is a continuation-in-part of Ser. No. 532,182, filed Sep. 14, 1983, now abandoned.

BACKGROUND OF INVENTION

This invention relates generally to periodontal compositions and methods; and relates more specifically to compositions and methods of this type which are capable of providing active oxygen in the oral cavity, to thereby inhibit the motility of harmful oral bacteria.

Recent developments in dental technology, coupled with topical fluorides, sealants and fluoridization of municipal water supplies, have fostered a remarkable decrease in tooth decay. While laymen have associated decay with the main cause of tooth loss, it is well-known to dental experts that the major cause of tooth loss after the age of 35, is in fact gum disease. Indeed, gum disease has now reached epidemic proportions—over 90% of the general population are considered by most such experts to suffer from some form of gum disease.

Since gum disease is not painful, it is easily undetected, and in consequence, untreated. Without the acute pain associated with a toothache, most people indeed pay little or no attention to their gums until the disease has reached an advanced stage and they are threatened by the loss of teeth.

Recent studies and investigations, however, have conclusively demonstrated that the major cause of gum disease is specific bacteria that live and thrive in the gum crevices. These bacteria give off toxins that attack the bone, cementum and gums which support the teeth. If one is able to eliminate the cause (bacteria), the result is healing of the gums.

Dentists and periodontists have long known that certain substances can exert powerful cleansing and sanitizing action on the teeth, the gums and the oral cavity. Hydrogen peroxide, baking soda (sodium bicarbonate), and salt (sodium chloride) are examples of such materials. The major recent proponent of an antimicrobial method based on such knowledge, is Dr. Paul Keyes; and indeed this new therapy is now widely recognized as the "Keyes Technique".

Prior to the popularization of Dr. Keyes methodology most periodontal cases were referred to periodontists, and the method of treatment was often surgery (gingivectomy). This surgery is expensive and painful. Because of the pain, suffering, and expense associated with gum surgery, a rapidly growing number of dentists are, however, now adopting the concept of Dr. Keyes, and his non-surgical approach to gum disease.

Instead of a scalpel, Keyes relies on such ordinary household items as salt, hydrogen peroxide and baking soda to create a hostile climate for these troublesome bacteria. The baking soda neutralizes the acidic toxins given off by the bacteria, and the peroxide effectively kills the anerobic bacteria that cause gum disease. The anerobic bacteria cannot survive in an oxygenated environment.

Unfortunately baking soda and peroxide must be mixed daily, because these two elements decompose rapidly when mixed together. This is a messy, time-consuming and unpleasant daily chore. As a result, it is very difficult for the potential beneficiaries of such therapy to faithfully adhere to the regimen.

The Keyes method is e.g. described in an article by Judith E. Randal in A.H. (March/April 1982), at pages 82-85, and elsewhere. According to the procedure, once a day a patient is required to perform the following routine:

(a) Two tablespoons or so of baking soda are wet with enough hydrogen peroxide to form a thick paste;

(b) A rubber tip, of the kind found on some toothbrush handles, is employed to massage the paste into the spaces between the teeth and at the gum margins on both the front and back sides of the teeth;

(c) Again using the paste, the patient messages the gums and gum margins front and back with an electric toothbrush or a child-sized manual toothbrush;

(d) Enough salt is added to a glass of warm water so that some remains in the bottom even when the solution is stirred;

(e) The liquid part of the mixture is poured into a Water Pik ®; and with the device set at moderate speed, the teeth and gums, front and back are rinsed; and (f) A glass of plain water is run through the Water Pik ® to prevent salt damage to its internal parts.

As is readily apparent from the above description of the Keys method, it is a relatively complex and burdensome procedure for an individual patient to employ on a daily basis. It would clearly be desirable for a patient to be able to perform the Keyes method or a method similarly effective in an easier manner, e.g., with a single composition.

However, merely combining the components employed by Keyes into a "prepackaged" formula will not provide an effective means for accomplishing the desired results. Specifically, the hydrogen peroxide and/or sodium bicarbonate can in a combination decompose rapidly. Hydrogen peroxide (or other peroxide) can break down in the presence of alkalinity, heat, light and/or metal ions as follows:

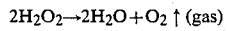

Similarly, sodium bicarbonate can break down in the presence of hydrogen peroxide, heat and/or water as follows:

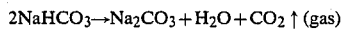

Since the active materials are lost or diminished, such a formula will have a short shelf life. Moreover, the gas evolution is especially undesirable with a tooth paste or gel, since such gas evolution can cause swelling and/or bursting of tubes or other packages containing same. All of these factors are undesirable for a consumer product.

SUMMARY OF INVENTION

Now in accordance with the present invention, a periodontal composition is provided, which includes a peroxide and a bicarbonate, in a single highly stable form, which is therefore susceptible to conventional modern packaging and dispensing systems, and which can be readily and effectively used by the consumer.

The composition can be prepared as a non-aqueous paste or gel dentifrice, and generally comprises a water soluble, non-aqueous vehicle having dispersed therein an orally acceptable organic or inorganic peroxide; and a bicarbonate salt. The composition is substantially anhydrous, and the amounts and relative proportions of the peroxide and bicarbonate are sufficient to provide a level of bactericidally active oxygen upon breakdown of the peroxide by tissue contact and by reaction with the bicarbonate in the oral cavity of the user. The amount of the bicarbonate is effective to provide a neutral or basic pH upon dissolution of the composition in water. The composition may be contacted with water in mouth saliva, a moistened toothbrush, or by contact with water from an oral irrigating device such as a Water-Pik ®. Also the composition can be directly disolved in a volume of water to provide a mouth wash.

At least one of the peroxide or bicarbonate is provided with a water-soluble barrier coating, which is, however, insoluble in the non-aqueous vehicle, to prevent reaction therebetween in the absence of water dissolution of the coating. All of the components of the composition thus far referred to are water-soluble, whereby upon the composition being contacted with substantial quantities of water, including in the oral cavity of a user, dissolution of the barrier coating enables reaction of the peroxide and bicarbonate to augment release of active oxygen, to inhibit the motility of oral bacteria in said cavity. Dissolution of the bicarbonate further, enables neutralizing of acid secretions in the oral cavity.

The compositions of the invention may also include one or more auxiliary stabilizers, which serve to further reduce the possibility of premature decomposition of the peroxide, or of premature raction between peroxide and bicarbonate components. These can comprise e.g. dessicants which remove or absorb any trace water which may find its way into the compositions. A preferred material for these purposes is colloidal pyrogenic silica, which also serves in the composition as a thickener.

The compositions may also include small amounts of normal dentrifice adjuvants, such as flavoring agents (typically 0.1 to 5%); cleansing and foaming agents (surfactants), typically as 0.1 to 10%; normally acceptable dental abrasives or polishing agents (preferably 1 to 15%, although higher amounts can be used), such as dicalcium phosphate, suitable calcined kaolins, etc.; sweetening agents, colorants and the like.

The compositions may also include fluorine-containing compounds as are known for use in the dentifrice art, such as sodium fluoride, sodium monofluorophosphate, stannous fluoride, and the like.

In order to afford yet further stability to the compositions of the invention, the dentifrice adjuvants and fluorine-containing compounds (if present), may be provided with water soluble barrier coatings, as described for the bicarbonate and/or peroxide components.

DETAILED DESCRIPTION OF INVENTION

The peroxide component of the compositins of the invention preferably comprises urea peroxide or hydrogen peroxide. If the latter is used it should preferably be absorbed on an orally acceptable inert particulate carrier, as for example a kaolin, which can then be provided with a water soluble barrier coating.

The peroxide component of the compositions of the invention is included in an amount sufficient to allow release of sufficient oxygen when the composition is contacted with water, e.g. during brushing of teeth, to inhibit the motility of oral bacteria, e.g., in the treatment of gingivitis. Typically, the peroxide can be employed in the composition of the present invention in amounts so that at least about 1% of the composition comprises a peroxide. Preferably, the peroxide comprises from about 1 to about 20% by weight of the composition. More preferably, the peroxide comprises from about 2 to about 5% by weight of the composition. A typical peroxide concentration in the composition is about 3% by weight. The active peroxide content (i.e., the equivalent of $H_2O_2$ in the peroxide employed) is preferably between about 0.5 and about 5% by weight, more preferably between about 1 and about 3% by weight.

The bicarbonate salts employed in the composition of the invention include any which are sufficiently soluble so that, when the composition is contacted with water, e.g., in the brushing of teeth, a neutral or basic pH is provided by the bicarbonate. Suitable bicarbonates include alkali metal and alkaline earth metal bicarbonates. Examples of suitable bicarbonates include sodium bicarbonate, potassium bicarbonate, lithium bicarbonate, calcium bicarbonate, magnesium bicarbonate, and the like or mixtures thereof. A preferred bicarbonate is sodium bicarbonate. If it is desirable, e.g., with a patient having high blood pressure, etc., sodium-free compositions or low sodium compositions can be employed, such as potassium bicarbonate or magnesium bicarbonate. Combinations of bicarbonate salts can also be employed, e.g. sodium and potassium bicarbonates.

The bicarbonate is included in the composition of the invention in an amount sufficient to provide a neutral and basic pH when the composition is contacted with water, (as is in the oral cavity), preferably a pH of from about 7.0 to about 9.5. The amount of bicarbonate actually employed in the method of the invention can vary greatly depending upon the form of the composition and its intended method of application. The bicarbonate preferably comprises from about 1 to about 20% by weight of the composition in a tooth paste or gel, more preferably from about 2 to about 8% by weight.

Of the bicarbonate and peroxide components of the present compositions, preferably at least the bicarbonate is provided with the water soluble barrier coating. Alternatively the peroxide along may be the member so provided; or to achieve still greater stability, both members can be provided with the said coating.

As mentioned, the water soluble barrier coatings can also be provided on desired species of the dentifrice adjuvants when such are present—for example, upon particulate surfactants such as sodium lauryl sulfate, upon dental abrasives or polishing agents such as dicalcium phosphate, upon fluorine-containing compounds, flavorings, colorants, etc. This in order to minimize any detrimental effects which such adjuvants might otherwise have upon the stability of the present compositions.

While not as important a factor where the bicarbonate is provided with a barrier coating, it has nonetheless been found in the present invention that by increasing the particle size of the bicarbonate salt, which decreases its surface area, the stability of the peroxide in the compositions of the invention is increased. For example, as among grade numbers 1, 2 and 5 baking soda available from Allied Chemical (Bulletin No. 513-016 U.S.A.), the No. 5 grade provides the greatest peroxide stability in the composition of the invention, while the No. 2 grade provides almost the same stability. Preferably, the particle size of the bicarbonate salt is such that it provides a residual peroxide level of from about 95 to about 99%, more prefrably, from about 97.5 to about 99%, when the composition is stored in a closed container at room temperature for about 6 weeks. Typical screen analysis of such grades of baking soda are set forth below:

| Screen Analysis | GRADE BAKING SODA | | |
|---|---|---|---|
| | No. 1 | No. 2 | No. 5 |
| Cumulative % on | | | |
| U.S. No. 60 | | | 1 |
| 80 | | trace | 37 |
| 100 | 1 | 1 | 72 |
| 170 | 25 | 68 | 98 |
| 200 | 38 | 89 | 100 |
| 71 | 99 | | |
| 325 | 71 | 99 | |
| Bulk Density (lb/ft$^3$) | 53 | 55 | 46 |

Preferably, the bicarbonate employed in the composition of the present invention has an average particle size of from about 100 to about 2,000 microns, more preferably from about 200 to about 800 microns.

The surface area of the bicarbonate particles in the composition of the invention can be further reduced by agglomerating the particles to form aggregates with less surface area than the component particles. These aggregates can in turn be coated. Aggregation and coating can also be conducted simultaneously or in sequence. Agglomeration can be accomplished by various means. For example, the bicarbonate salt particles can be mixed together with, for example, a polyethylene glycol of suitable molecular weight. Depending upon the amount of polyethylene glycol employed, the resulting material can be in the form of agglomerted particles or in the form of a thick and extrudable paste. In the case of such a paste, the paste like material can be extruded into thin strips and then cut into small pellets containing agglomerated particles of the bicarbonate salt. Such agglomerated sodium bicarbonatee salt particles preferably have an average particle size in the range of from about 100 to about 2,000 microns and can be used in the same manner as the normal bicarbonate salt in the compositions of the invention.

It should be pointed out here that relatively small amounts of chemical decomposition of the peroxide and/or bicarbonate during storage can give rise to large amounts of gases (oxygen and/or carbon dioxide) which can cause a closed container such as a tooth paste tube to swell or even explode. It has been found that in the absence of the barrier coating and/or auxiliary stabilizer used in the present invention such gas evolution does, in fact, take place and can cause such swelling, etc. The present invention overcomes this problem by including a suitable stabilizer—i.e. a barrier coating—which prevents breakdown of the peroxide and/or bicarbonate.

The barrier coating preferably comprises a water-soluble, edible and non-toxic polymer or gum. Edible and water soluble plant gums and mucilages are generally suitable for the foregoing purposes. Heteropolysaccharides are the predominant constituents of these latter products. Among such useable natural gums and mucilages are guar gum, xanthate gum, gum arabic, and gum tragacanth. Also utilizable are locust bean gum and carob bean gum as well as gelatin, pectin, and cellulose derivatives such as Klucel ®. High molecular weight polyethylene glycols are also suitable, such as the products of this type sold under the trademarks CARBOWAX by Union Carbide.

Further, synthetic polymers having the aforementioned properties can also be used. These include cellulosic polymers such as methyl cellulose and carboxy methyl cellulose of appropriate molecular weights; as well as other similar cellulosic polymeric compounds.

In a presently preferred form of barrier coating, an edible non-toxic water soluble starch or starch-like polymer or a gum is coated upon at least the bicarbonate, so as to effectively form a barrier layer or protective shielding about the particles of same. Typically, the said coating comprises from about 1 to 30% by weight of the bicarbonate, more preferably from about 5 to 15%, and still more preferably about 10% by weight of the bicarbonate. A suitable starch-coated product of this type is available from Durkee Corporation under product designations such as "ML 90". These commercially available products constitute sodium bicarbonate coated with a water soluble malto-dextrin (partially broken down), and have heretofore found use as leavening in the baking industry.

More generally, starches are natural polysaccharides, which are usually regarded as homopolysaccharides. A typical starch is thus a cryst polymeric compound consisting of about 27% linear polymer (amylose) and 73% branced polymer (amylopectin). By hydrolysis, derivatives are obtained, such as the mentioned malto-dextrin, amylodextrin, or amylogen etc., which are referred to as "water soluble starches", and which are utilizable as the present barrier coatings.

Commercially, water soluble starches of this type are available under such tradenames as CAPSUL, STARCH 46, and N-LOK, all of these being products of National Starch Company.

The barrier coating can be provided alternatively upon the peroxide component, or can be provided on both peroxide and bicarbonate. Where the peroxide is a solid powder such as the preferred urea peroxide, the coating may be directly applied. Where a normally liquid peroxide is used, i.e. such as hydrogen peroxide, the latter is first sorbed on an inert carrier such as a kaolin, which is then coated with the barrier coating. The amount of coating material where same is applied to the peroxide component is typically in the ranges indicated for the coatings on the bicarbonate.

It should be understood that the barrier coatings of the present invention, depending upon the mode of application upon the protected species, may encapsulate the latter, or may form a protective coating by being clustered about the particles of the protected species. In any event, the active species is thereby covered by the coating and effectively isolated from undesired interactions, until released by water disrupting the said barrier.

The provision of a barrier coating upon the active species can be carried out by numerous known methodologies. Typically, the actives in the form of powders, for example, sodium bicarbonate and/or urea peroxide can be so coated while suspended in air in a fluidized bed procedure. The coatings may be applied in the form of a solution (aqueous, non-aqueous or hydroalcoholic) or as a melt—that is sprayed on the particles to be coated. Among the major types of spraying procedures which can be so used are top spraying; Wurster spraying or rotor spraying. Details of suitable coating methodology can be found in a commercial brochure published by the Glatt Company of Ramsey, NJ, which is authored by Mehta and Jones and entitled "Coated Pellets Under the Microscope". In the top spray method, the coating solution is sprayed downwardly onto the substrate as it is fluidized by air flowing from below.

Coating of the active species with the barrier coating can also be effected by other generally known methods. Thus, for example, the actives in the form of dry powders (e.g. sodium bicarbonate, urea peroxide) can be dry mixed or rolled with the gum or polymer. It is also possible to melt the polymer or gum and coat the actives by spraying or rolling or intermixing. Melting e.g. can also be used to apply coatings of sugars (sucrose and dextrose), dry sorbital and powdered mannitol.

Where particulate dentifrice adjuvants are to be similarly provided with barrier coatings (e.g. foaming agents, surfactants such as sodium lauryl sulfate or dental abrasives such as dicalcium phosphates, flavorings, fluorine compounds, colorants, etc.), the same techniques may be used for providing the coating—notably spraying the coating onto the suspended particulates in a fluidized bed.

The hydrophilic, non-aqueous vehicles employed in the tooth paste or gel composition of the present invention are water soluble so that they facilitate the action of the bicarbonate and peroxide during brushing with the composition. Thus, the vehicles employed in the present invention preferably rapidly dissolve with water when used by a consumer, e.g., in mouth rinse water or the water in a pre-moistened toothbrush in saliva, or in the post-brushing wate rinse. The active species, i.e., the peroxide and bicarbonate salt, may be dispersed, or suspended in the vehicle.

Suitable hydrophilic, non-aqueous vehicles for use in the present invention include polyalkylene glycols, non-ionic surfactants, anionic surfactants, ampholytic surfactants, cationic surfactants and alkanolamides. Also suitable are glycerol, propylene glycol or sorbitol in combination with silica, clay, polymer and/or gum thickeners, and perhaps dicalcium phosphate as a cleansing agent.

The hydrophilic, non-aqueous vehicles preferably provide a viscosity for the composition suitable for its use as a toothpaste or gel, e.g. between about 2,000 cps. to about 200,000 cps. If the selected vehicle does not itself provide the desired viscosity, viscosity modifiers, such as barrier coated dicalcium phosphate, finely divided pyrogenic silica and the like may be added, and/or other known and orally acceptable vehicle agents can be included to provide such desired viscosity.

Typically, the hydrophilic, non-aqueous vehicles employed in the tooth paste or gel compositions of the invention are present in an amount of from about 45 to about 90% by weight. Preferably, the vehicles are present in an amount of from about 85 to about 90%.

Suitable polyalkylene glycols for use as vehicles in the present composition include those having molecular weights of from about 200 to about 20,000. Such materials range in physical state from thin liquids to pastes to solids with increasing molecular weight.

Preferred polyalkylene glycols for use as vehicles in the present invention are polyethylene glycols having the general formula H(OCH₂CH₂)ₙOH, where n is greater than or equal to 4. These liquid and solid polymers are widely known and available under trademarks such as Carbowax ® (Union Carbide). In general, each polyethylene glycol (PEG) is identified by the manufacturer by a number which corresponds to its average molecular weight, e.g. "Carbowax ® 400". Preferred PEG's for use in the present invention have a molecular weight in the range of from about 400 to about 8,000. Mixtures of such polyethylene glycols of differing molecular weights (and for that matter other vehicles discussed herein) can be employed to provide desirable viscosity characteristics for the composition.

Other suitable polyalkylene glycol vehicles include materials of the formula

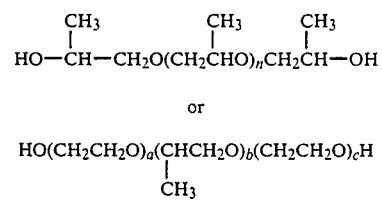

or

HO(CH₂CH₂O)ₐ(CHCH₂O)ᵦ(CH₂CH₂O)ᶜH
　　　　　　　　　|
　　　　　　　　CH₃ wherein n, a, b and c are integers such that the molecular weights of such materials are in the range of from about 1,100 to about 14,000. Also suitable are the polyoxyalkylene derivatives of ethylene diamine, e.g., the materials sold under the trademark TETRONIC.

Suitable non-ionic surfactants for use as the hydrophilic, non-aqueous vehicle in the tooth paste or gel composition of the invention include materials such as polyoxyethylene sorbitan fatty acid esters, e.g., materials sold under the trademark TWEEN. Examples of such materials are polyoxyethylene (20) sorbitan monolaurate (TWEEN 20), polyoxyethylene (20) sorbitan monopalmitate (TWEEN 40), polyoxyethylene (20) sorbitan monostearate (TWEEN 60), polyoxyethylene (4) sorbitan monostearate (TWEEN 61), polyoxyethylene (20) sorbitan tristerate (TWEEN 65), polyoxyethylene (20) sorbitan monooleate (TWEEN 80), polyoxyethylene (5) Sorbitan monooleate (TWEEN 81), and polyoxyethylene (20) sorbitan trioleate (TWEEN 85).

Polyoxyethylene fatty acid esters are also suitable for use as the vehicle in the tooth paste composition of the invention. Examples include those materials sold under the trademark MYRJ such as polyoxyethylene (8) stearate (MYRJ 45) and polyoxyethylene (40) stearate (MYRF 52).

Another suitable class of non-ionic surfactants for use in the vehicle in the present invention are polyoxyethylene fatty ethers, e.g., the materials sold under the trademark BRIJ. Examples of such materials are polyoxyethylene (4) lauryl ether (BRIJ 30), polyoxyethylene (23) lauryl ether (BRIJ 35), polyoxyethylene (2) cetyl ether (BRIJ 52), polyoxyethylene (10) cetyl ether (BRIJ 56), polyoxyethylene (20) cetyl ether (BRIJ 58), polyoxyethylene (2) stearyl ether (BRIJ 72), polyoxyethylene (10) stearyl ether (BRIJ 76), polyoxyethylene (20) stearyl ether (BRIJ 78), polyoxyethylne (2) oleyl ether (BRIJ 93), polyoxyethylene (10) oleyl ether, and polyoxyethylene (20) oleyl ether (BRIJ 99).

In one embodiment of the invention, a portion of a non-ionic surfactant employed in the vehicle in the composition of the invention can be substituted with a lipophilic surfactant, e.g., sorbitan fatty acid esters such as the materials sold under the trademark ARLACEL. Suitable lipophilic surfactants include sorbitan monolaurate (ARLACEL 20), sorbitan monopalmitate (ARLACEL 40), sorbitan monostearate (ARLACEL 60), sorbitan monooleate (ARLACEL 80), sorbitan sesquioleate (ARLACEL 83), and sorbitan trioleate (ARLACEL 85). Typically, from about 10 to about 90% of the non-ionic surfactant can be substituted by a lipophilic surfactant, preferably from about 25 to about 50%.

As noted above, other classes of surfactants such as cationic surfactants, anionic surfactants, ampholytic surfactants and alkanolamides can also be employed as the vehicle in the composition of the present invention. Such materials can be employed either by themselves as the vehicle or together with a polyakylene glycol or a non-ionic vehicle as discussed above. Examples of suitable anionic, cationic, ampholytic and alkamolamide surfactants include di-tallow dimethyl ammonium chloride, sodium lauryl sulfate, the material

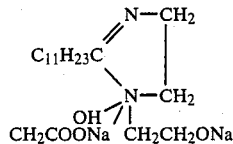

sold under the trademark MIRANOL, and coconut alkanolamide. Typically, when these materials are used as part of the vehicle, they are substituted for from about 10 to about 90% by weight, preferably from about 25 to about 50% by weight, of the main vehicle used in the composition, e.g., a polyalkalene glycol or a non-ionic surfactant as discussed above.

Auxiliary stabilizers can also be included in the compositions of the invention in order to augment stabilization of the bicarbonate, and especially of the peroxide componenet. These can comprise dessicating agents to absorb trace water, or can comprise chemical stabilizers.

Any orally acceptable material that stabilizes the peroxide during storage of the composition in a closed container can e.g. be employed as an auxiliary stabilizer in the present composition. Examples of suitable such stabilizing agents include desicating agents, sequestering agents, colloidal particles, free radical preventatives, inorganic hardness salts, acidulating agents, and mixtures of such stabilizing agents.

Examples of suitable dessicating agents include magnesium sulfate, sodium sulfate, calcium sulfate, calcium chloride and colloidal silica, e.g., colloidal silica particles sintered together in chainlike formations having surface areas of from about 50 to about 400 square meters per gram such as materials sold under the trademark Cab-O-Sil ® by Cabot Corp. It is believed that such materials act to stabilize the compositions of the invention by, for example, absorbing any existing water either present in or contacted with the composition so as to further preclude breakdown of the peroxide and/or bicarbonate.

Colloidal pyrogenic silica serves a further purpose in the present compositions, i.e. it is a well-recognized thickener, and is very useful in achieving a desired consistency for both practical and aesthetic reasons.

Examples of suitable sequestering and/or chelating agents include ethylene diamine tetraacetic acid (EDTA) or its sodium salts, nitrilotriacetic acid or its sodium salts, diethylene triamine pentaacetic acid (DTPA), or DEQUEST phosphonates available from Monsanto. It is believed that such chelating or sequestering agents stabilize the compositions of the invention, for example, by tying up metal ions such as $Fe^{+3}$, $Mn^{+2}$, $Cu^{+2}$, etc. that can catalyze the decomposition of peroxide in the compositions.

Other effective auxiliary stabilizers for use in the present composition include in addition to the colloidal particles such as the pyrogenic silica mentioned above, finely divided clays, zeolites and insoluble metallic oxides, e.g., magnesium and aluminum oxide. The pyrogenic silica materials are a preferred auxiliary stabilizing agent in the compositions of the present invention.

Also, free radical inhibitors or preventatives such as butyl hydroxytoluene, butyl hydroxyanisole and beta carotene can also reduce the instability of peroxide in the composition of the invention.

Inorganic hardness salts such as calcium or magnesium inorganic compounds also reduce peroxide instability. Examples of such compounds include magnesium carbonate, magnesium chloride, calcium sulfate, calcium chloride and the like.

The addition of anhydrous acidulating agents or their salts (powdered or granulated), also provide improvement in peroxide stability in the compositions of the invention. Examples of suitable acidulating agents for use in the present invention include ascorbic acid, tartaric acid, phosphoric acid as well as the chloride, sulfate or nitrate salts of calcium, magnesium or ammonium.

The inclusion of an auxiliary stabilizing agent in the composition of the present invention has been found to provide increased stability of the compositions in comparison to compositions without such stabilizing agent. For example, when 5% by weight of pyrogenic colloidal silica (Cab-o-sil ® M-5) was employed in combination with 10% by weight baking soda and 10% by weight urea peroxide in a polyethylene glycol 600 vehicle (remainder), a 96% residual peroxide level was found after storage of the composition in a closed container for 18 days at room temperature. By contrast, with a similar composition omitting the pyrogenic colloidal silica, only a 90% residual peroxide level was obtained under the same conditions. Typically, the auxiliary stabilizing material is included in the compositions of the present invention in an amount of from 0.1 to about 7.5%, preferably from about 1 to about 5%. For example, when pyrogenic colloidal silica materials are used as an auxiliary stabilizing agent (and thickener), suitable amounts thereof are from 1 to about 7.5% by weight, preferably from about 3 to about 5% by weight.

One embodiment of the invention and composition also includes chloride and/or sulfate salts such as alkali metal chlorides or sulfates, alkaline earth metal chlorides or sulfates, or mixtures thereof. Suitable chloride salts for use in the composition of the invention include sodium chloride, potassium chloride, lithium chloride, calcium chloride, magnesium chloride, sodium sulfate, potassium sulfate, magnesium sulfate, etc.

Typically, the chloride salts or other salts are included in the composition of the present invention in amounts of from about 1 to about 50% by weight of the composition. Preferably, the chloride or other salts are included in an amount of from about 1 to about 15% by weight of the composition.

The compositions of the invention can include many other components which are conventional in the art, again depending upon the ultimate use to be made of the composition. As with all the components of the composition, these components should preferably be of the class generally recognized as safe, especially for use in the mouth. For example, the composition of the invention can include conventional adjuvants, e.g., colorants, flavors, sanitizing agents, dentally acceptable abrasives, cleansing agents, and the like.

The compositions of the present invention can be prepared by methodology conventional in the art. For example, the peroxide material (either coated or encapsulated, sorbed on a solid material or a solid material itself) can be physically mixed with the (preferably) coated bicarbonate salt, and any other materials to be included in the compositions of the invention, such as a chloride salt or other carriers and/or adjuvants. The composition can be prepared into a paste or gel again in a manner conventional for preparing such paste or gels as is well-known in the art by merely including the desired amount of the peroxide, auxiliary stabilizer (if used) and bicarbonate in the desired hydrophilic, non-aqueous vehicle. As noted above, the paste or gel is non-aqueous.

In a preferred method of preparing a composition of the present invention, an auxiliary stabilizer and thickener such as a pyrogenic colloidal silica material, is first mixed with the hydrophlic, non-aqueous vehicle, such as polyalkylene glycol, e.g. of polyethylene glycols such as Carbowax ®400 and Carbowax ®8,000. Additonal surfactants can also be present to provide good foaming when used in the mouth. To such mixture is added the peroxide, such as urea peroxide with stirring. The peroxide can as noted above, be optionally coated with the barrier coating. the bicarbonate salt is then added to the mixture containing the peroxide. The bicarbonate salt can likewise be (and preferably is) pre-coated as discussed above. Other desired adjuvants can be added at the tail end of this process, some of which adjuvants may be provided with a water soluble barrier coating as already indicated.

The dentifrice adjuvants (foaming agent(s), flavor(s), colorant(s), dentifrice abrasive(s), fluorine-containing compound(s) etc.) may likewise be provided with a water-soluble coating, either by treating same alone or in combination, or by treatment together with the peroxide and/or with the bicarbonate. The coated dentifrice adjuvants may be incorporated in the vehicle when not combined with the peroxide or bicarbonate.

The compositions of the present invention as noted above can be used to treat periodontal disease. In such treatment, it is believed that the composition of the invention attacks the anerobic bacteria that cause such periodontal disease. In the method of the present invention, the compositions described above are applied to the gums of the patient, e.g., a mammal such as man, in an amount effective to inhibit the bacterial motility of the oral anerobic bacteria and other bacterial types.

The invention is further illustrated by the following Examples, which are, however, intended to be illustrative, and not delimitive of the invention which is otherwise set forth:

EXAMPLE I

A composition in accordance with the present invention is prepared in the form of a paste or gel. A high molecular weight polyethylene glycol, Carbowax ®8,000, is warmed and combined with a low molecular weight polyethylene glycol, Carbowax ®400. This mixture is stirred and Cab-o-sil ®M-5 is added thereto and mixed therewith. Baking soda pre-coated with 10% of an edible non-toxic water soluble starch is used in this formulation. Urea peroxide is added to the polyethylene glycol/Cab-o-sil ® mixture and stirred. Then the coated baking soda is added with stirring. Suitable flavoring agents and a foaming agent, MAPROFIX 563, is added to and mixed with the resulting mixture. The mentioned surfactant is a purified oral grade of sodium lauryl sulfate. The weight percent of the respective ingredients in the composition of this Example are listed below:

| Ingredient | % by Weight |
|---|---|
| Polyethylene glycol 8,000 (Carbowax ® 8,000) | 14.9 |
| Polyethylene glycol 400 (Carbowax ® 400) | 75.4 |
| Pyrogenic colloidal silica (Cab-o-Sil M-5) | 1.8 |
| Urea Peroxide (Rebecco) | 3.5 |
| Coated Baking Soda (Durkee MC-90 - 10% coating by weight,) | 3.9 |
| Flavoring agents | 0.5 |
| Surfactant - sodium lauryl sulfate (Maprofix 563 - Onyx-Chemical Co.) | 0.5 |

This toothpaste (or "gel") is a cosmetically acceptable dentifrice which produces bactericidally active oxygen in use. The composition is "package stable" (as generally recognized) under reasonable conditions of storage when packaged in a squeeze tube or pump-type of container; i.e. the formation of gases ($CO_2$ and $O_2$) that would otherwise occur in a single phase unstabilized composition of peroxide and bicarbonate is effectively inhibited. Typical test procedures for confirming such package stability involves subjecting the composition in a closed container to 3 weeks storage at 105° C.

EXAMPLE II

In this Example, a further paste or gel similar to that of Example I is prepared, wherein the respective ingredients are as follows:

| Ingredient | % by Weight |
|---|---|
| Polyethylene glycol 8,000 (Carbowax ® 8,000) | 11.0 |
| Polyethylene glycol 400 (Carbowax ® 400) | 76.24 |
| Pyrogenic colloidal silica (Cab-o-Sil M-5) | 3.5 |
| Urea Peroxide (Rebecco) with 10% coating by weight | 3.9 |
| Baking Soda (Church & Dwight) Grade 5, with 10% coating by weight | 3.9 |
| Flavoring agents | 1.9 |
| Surfactant foaming agent - sodium lauryl sulfate | 0.56 |

Both the urea peroxide and the baking soda are provided with a coating of 10% by weight of maltodextrin (Lodex 10 product of Durkee Foods) by being sprayed with an aqueous solution of the said product as the particulate peroxide and baking soda are maintained in a fluidized bed. The final composition is again a package stable, cosmetically acceptable dentifrice which produces bactericidally active oxygen in use.

The flavoring agents can include known dentifrice adjuvants, such as methyl salicilate, menthol, sodium sacharin (or other sweeteners, e.g. Nutrisweet ®), and colorants. Also, conventional dentifrice abrasives and fluorine-containing compounds can be provided.

EXAMPLE III

A dentifrice paste or gel similar to that of Example II is prepared, except that the foaming agent (sodium lauryl sulfate) is also provided with a 10% coating of maltodextrin, which tends to further augment stability in the final product. The method of coating is as aforementioned, i.e. by spraying the coating onto the powdered agent while same is suspended in a fluidized bed. The resulting dentifrice has characteristics as in Example II. The foaming agent can typically be present from about 0.1% to about 10.0%, with the proportion of the vehicle being suitably adjusted.

EXAMPLE IV

A dentifrice paste or gel similar to that of Example III is prepared, except that 10% dicalcium phosphate is added as a dental abrasive, (more generally 1-50% of an abrasive can be used, with 1-15% being preferable), with the weight percent in the total composition of the vehicle (i.e. glycol 8,000 and glycol 400) being adjusted accordingly. The dicalcium phosphate is coated in advance with 10% maltodextrin, as described for the foaming agent in Example III, in order to maintain and augment stability in the final product. The resulting dentifrice has characteristics, including stability, as in Examples II and III.

EXAMPLE V

A dentifrice paste or gel similar to Example IV is prepared, except that the dentifrice "adjuvant package" is as follows:

| Ingredient | % by weight of total composition |
| --- | --- |
| foaming agent-sodium lauryl sulfate | 1.0 |
| dental abrasive-dicalcium phosphate | 10.0 |
| Flavor mix | 3.0 |
| Sweetener-sodium sacharine | 0.3 |

The adjuvants are provided with a 10% by weight barrier coating as in Example IV. The vehicle proportion is adjusted to provide a 100% total. The resulting dentifrice has characteristics including stability, as in Example IV.

EXAMPLE VI

A dentifrice paste or gel similar to that of Example II is prepared except that the barrier coating is provided by spraying the actives to provide a 10% by weight coat of Methocel ®, e.g. Methocel E-4M. The resulting dentifrice has stability as in Examples II and III.

EXAMPLE VII

Dentifrice pastes or gels are prepared similar to Example II, but wherein water soluble barrier coatings on the actives (urea peroxide and sodium bicarbonate) are provided by spraying on 10% by weight coatings of the Capsul ®, Starch 46 ®, and N-LOK ® soluble starch products of National Starch. The resulting dentifrices have stabilizers as in Examples II and III.

EXAMPLE VIII

Dentifrice pastes or gels are prepared similar to Example II, except that water soluble barrier coatings on the actives (urea peroxide and sodium bicarbonate) are provided by spraying on 10% by weight coatings of guar gum, sodium alginate and kelginate gum polymer from aqueous solutions of same. The finally resulting dentifrices have stabilities as in Examples II and III.

The following Examples IX and X illustrate the advantages of utilizing auxiliary stabilizers and/or alternate vehicles. In each instance a toothpaste or gel composition was prepared by mixing together the indicated auxiliary stabilizer with the vehicle component(s). The peroxide and then the bicarbonate salt are mixed in with the stabilizer vehicle mixture. The actives and adjuvants in these Examples can be coated in accordance with the invention to provide greater stability.

EXAMPLE IX

This composition is prepared in the form of a paste or gel. A polyethylene glycol 600 is warmed and combined with a polyethylene glycol 400. This mixture is stirred and Cab-o-sil ® M-5 is added thereto and mixed therewith. Urea peroxide is added to the polyethylene glycol/Cab-o-sil ® mixture and stirred. The baking soda (Grade 5 from Church and Dwight) is added with stirring. Suitable flavoring agents and sodium chloride are added to and mixed with the resulting mixture. The weight percent of the respective ingredients in the composition of the invention are listed below.

| Ingredient | % by Weight |
| --- | --- |
| Polyethylene glycol 400 (Sentry Grade) | 33% |
| Polyethylene glycol 600 (Sentry Grade) | 45% |
| Pyrogenic colloidal silica (Cab-o-Sil M-5) | 7.5% |
| Urea Peroxide | 3.5% |
| Baking Soda (Grade 5 from Church and Dwight) | 3.5% |
| Flavoring agents, foaming agents, and dental abrasive | 6.5% |
| Sodium chloride | 1.0% |

This toothpaste has a commercial consistency and chemical stability (determined by permanganimetric titration) that is over 88% stable with respect to peroxide at 105° for one month and 29% stable at 120° F. for one month. The conventional addition of normal flavoring agents provides the paste with a conventional tooth paste-like taste.

EXAMPLE X

A series of toothpaste compositions is prepared by the general procedure described in Example IV above employing the ingredients listed below in the indicated proportions:

| Ingredients | % by Weight |
| --- | --- |
| NaHCO$_3$ | 3.5 |
| Urea Peroxide | 3.5 |
| Polyethylene glycol 400 (40%) \} vehicle | 88 |
| Polyethylene glycol 600 (60%) | |
| Magnesium Sulfate Anhydrous powder | 5 |

Anhydrous sodium sulfate, calcium sulfate or calcium chloride can be substituted for the magnesium sulfate in the above formulation.

| Ingredients | % by Weight |
| --- | --- |
| NaHCO$_3$ | 3.0 |
| Urea Peroxide | 3.1 |
| Polyethylene glycol 400 (40%) | |

| Ingredients | | % by Weight |
|---|---|---|
| Polyethylene glycol 600 (60%) | } vehicle | 87.4 |
| EDTA | | 2.0 |
| Cab-o-sil M-5 | | 4.5 |

Nitrilotriacetic acid (or its salts), diethylene triamine pentaacetic acid (or its salts), or Dequest phosphate chelating agents can be substituted for the ethylene diamine tetracetic acid (EDTA) in the above formulation.

| Ingredients | | % by Weight |
|---|---|---|
| Urea Peroxide | | 2.7 |
| NaHCO$_3$ | | 2.7 |
| Cab-o-Sil M-5 | | 4.0 |
| Polyethylene glycol 400 (40%) | } vehicle | 88.1 |
| Polyethylene glycol 600 (60%) | | |
| Magnesium oxide | | 2.5 |

Finely divided (colloidal) clays, zeolites and other insoluble metallic oxides such as aluminum oxide can be substituted for magnesium oxide in the above formulation.

| Ingredients | | % by Weight |
|---|---|---|
| Urea Peroxide | | 2.0 |
| NaHCO$_3$ | | 2.0 |
| Cab-o-Sil ® M-5 | | 3.0 |
| Polyethylene glycol 400 (40%) | } vehicle | 92.0 |
| Polyethylene glycol 600 (60%) | | |
| Butyl hydroxytoluene | | 1.0 |

Butyl hydroxyanisole or beta carotene can be substituted for the butyl hydroxytoluene in the above formulation.

| Ingredients | | % by Weight |
|---|---|---|
| Urea Peroxide | | 3.1 |
| NaHCO$_3$ | | 3.1 |
| Cab-o-Sil ® M-5 | | 4.5 |
| Polyethylene glycol 400 (40%) | } vehicle | 84.3 |
| Polyethylene glycol 600 (60%) | | |
| Magnesium carbonate | | 5 |
| Urea Peroxide | | 2.5 |
| NaHCO$_3$ | | 2.5 |
| Cab-o-Sil M-5 | | 4.2 |
| Anhydrous Citric Acid | | 0.5 |
| Polyethylene glycol 400 (40%) | } vehicle | 91.3 |
| Polyethylene glycol 600 (60%) | | |

Absorbic acid, tartaric acid, phosphoric acid as well as the chloride, sulfate, nitrate salts of calcium, magnesium and ammonium may be substituted for the anhydrous citric acid in the above formulation.

| Ingredients | % by Weight |
|---|---|
| Urea Peroxide | 3.75 |
| NaHCO$_3$ | 3.75 |
| Polyoxypropylene polyoxyethylene glycol (PLURONIC L-72) | 85 |
| Cab-o-sil ® M-5 | 7.5 |

PLURONIC-25R may be substituted for PLURONIC L-72 in the above formulation.

| Ingredients | % by Weight |
|---|---|
| Urea Peroxide | 3.0 |
| NaHCO$_3$ | 3.0 |
| Polyoxyethylene (20) sorbitan monooleate (Tween 80) | 88.0 |
| Cab-o-sil ® M-5 | 6.0 |

Polyoxyethylene (2) steryl ether (BRIJ 72) or polyoxyethylene (8) sterate (MYRI 45) may be substituted for TWEEN 80 in the above formulation. In additin, a portion of the TWEEN 80, e.g., one-half, may be substituted with polyethylene glycol 600.

| Ingredients | % by Weight |
|---|---|
| Urea Peroxide | 3.5 |
| NaHCO$_3$ | 3.5 |
| Polyoxyethylene (20) Sorbitan monooleate (TWEEN 80) | 60.0 |
| Sorbitan Monooleate (Arlacel 20) | 26.0 |
| Cab-o-sil ® M-5 | 7.0 |
| Calcium Peroxide | 4.0 |
| NaHCO$_3$ | 4.0 |
| Cab-o-sil ® M-5 | 7.0 |
| Di-tallow dimethyl ammonium chloride | 10.0 |
| Polyethylene glycol 600 | 75.0 |

An anionic surfactant such as sodium lauryl sulfate, an ampholytic surfactant such as Miranol ®, or an alkanolamide such as coconut alkanolamide may be substituted for the di-tallow dimethyl ammonium chloride in the above formulation.

| Ingredients | % by Weight |
|---|---|
| Magnesium Peroxide | 5.0 |
| Potassium bicarbonate | 3.0 |
| PLURONIC L-72 | 84.5 |
| Cab-o-sil ® M-5 | 7.5 |

The above formulation can also be prepared by replacing half of the PLURONIC L-27 with polyethylene glycol 400 or polyethylene glycol 600.

The above formulations in this Example illustrate the various auxiliary stabilizers and vehicles that can be used either alone or in combination in the compositions of the present invention.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

We claim:

1. A non-aqueous paste or gel dentifrice composition, comprising:
   a water soluble, non-aqueous vehicle selected from the group consisting of polyalkylene glycols, polyoxyalkylene derivatives of ethylene diamine, polyoxyethylene fatty acid esters, non-ionic surfactants, anionic surfactants, ampholytic surfactants, cationic surfactants, alkanolamides, thickened glycerol, propylene glycol or sorbitol, and mixtures thereof, having dispersed therein (a) an orally acceptable organic or inorganic peroxide; and (b) a bicarbonate salt;
   said composition being substantially completely anhydrous; the quantities and relative proportions of said peroxide and bicarbonate being sufficient to provide quantities of bactericidally active oxygen upon breakdown of said peroxide by tissue contact and/or by reaction with said bicarbonate in the oral cavity; the amount of said bicarbonate being effective to provide a neutral or basic pH upon dissolution of said composition in water; and
   at least one of said peroxide or bicarbonate being provided with a water-soluble barrier coating which is insoluble in said vehicle selected from the group consisting of guar gum, xanthate gum, gum arabic, gum tragacanth, locust bean gum, carob bean gum, gelatin, pectin, cellulosic polymers, polyethylene glycols, a water soluble starch, and mixtures thereof, to prevent reaction therebetween in the absence of water dissolution of said coating; whereby upon said composition being contacted with substantial quantities of water, including in the oral cavity of a user of said composition, dissolution of the said barrier coating enables reaction of said peroxide and bicarbonate to augment release of said active oxygen, to inhibit the motility of oral bacteria in said cavity, and dissolution of said bicarbonate enables neutralizing of acid secretions in the said oral cavity.

2. A composition in accordance with claim 1, wherein said peroxide comprises urea peroxide.

3. A composition in accordance with claim 1, wherein said peroxide comprises hydrogen peroxide which is absorbed on an orally acceptable inert particulate carrier; said water soluble coating being applied at least onto said carrier.

4. A composition in accordance with any of claims 1, 2, or 3, wherein said barrier coating comprises a water soluble edible and non-toxic polymer.

5. A composition in accordance with any of claims 1, 2, or 3, wherein said barrier coating comprises a water soluble starch.

6. A composition in accordance with any of claims 1, 2, or 3, wherein said barrier coating comprises a water soluble gum.

7. A composition in accordance with any of claims 1, 2, or 3, wherein said barrier coating is provided upon both said bicarbonate and said peroxide.

8. A composition in accordance with claims 1, 2 or 3, wherein said peroxide comprises from about 1 to 3% by weight of said composition expressed as equivalents of $H_2O_2$, and said bicarbonate from about 2 to 8% by weight of said composition.

9. A composition in accordance with any of claims 1, 2, or 3, further including an auxiliary stabilizer for further inhibiting decomposition of said peroxide and premature reaction between said peroxide and bicarbonate.

10. A composition in accordance with any of claims 1, 2, or 3, further including from 1 to 7½% by weight of colloidal silica, for absorbing trace water in said composition to further stabilize same, and for acting as a thickener for said composition.

11. A composition in accordance with any of claims 1, 2 or 3, further including from 1 to 15% by weight of dicalcium phosphate, as a dental abrasive.

12. A composition in accordance with any of claims 1, 2 or 3 further including from 0.25 to 5.0% by weight of a foaming agent.

13. A non-aqueous paste or gel dentrifrice composition, comprising:
   a water-soluble, non-aqueous vehicle selected from the group consisting of polyalkylene glycols, polyoxyalkylene derivatives of ethylene diamine, polyoxyethylene fatty acid esters, non-ionic surfactants, anionic surfactants, ampholytic surfactants, cationic surfactants, alkanolamides, thickened glycerol, propylene glycol or sorbitol, and mixtures thereof, having dispersed therein (a) an orally acceptable organic peroxide; (b) a bicarbonate salt; and (c) as a desiccant and auxiliary stabilizer, from 1 to 7½% by weight of said composition, of colloidal silica;
   said composition being substantially completely anhydrous; the quantities and relative proportions of said peroxide and bicarbonate being insufficient to provide quantities of bactericidally active oxygen upon breakdown of said peroxide by tissue contact and/or by reaction with said bicarbonate in the oral cavity;
   the amount of said bicarbonate being effective to provide a neutral or basic pH upon dissolution of said composition in water;
   at least one of said peroxide or bicarbonate being provided with a water-soluble barrier coating which is insoluble in said vehicle, selected from the group consisting of guar gum, xanthate gum, gum arabic, gum tragacanth, locust bean gum, carob bean gum, gelatin, pectin, cellulosic polymers, polyethylene glycols, a water soluble starch, and mixtures thereof, to prevent reaction therebetween in the absence of water dissolution of said coating; whereby upon said composition being contacted with substantial quantities of water, including in the oral cavity of a user of said composition, dissolution of the said barrier coating enables reaction of said peroxide and bicarbonate to augment release of said active oxygen, to inhibit the motility of oral bacteria in said cavity, and dissolution of said bicarbonate enables neutralizing of acid secretions in the said oral cavity.

14. A composition in accordance with claim 13, wherein both said peroxide and bicarbonate are provided with said barrier coating.

15. A composition in accordance with claim 13, further including from about 10% by weight of a particulate water-soluble foaming agent.

16. A composition in accordance with claim 13, further including from about 1 to 15% by weight of a particulate dental abrasive.

17. A composition in accordance with claims 13 or 14, further including 0.1 to 10.0% by weight of a particulate foaming agent which is provided with a water-soluble barrier coating.

18. A composition in accordance with claims 13 or 14, further including from about 1 to 50% by weight of a particulate dental abrasive which is provided with a water-soluble barrier coating.

19. A composition in accordance with claim 13, wherein said peroxide is urea peroxide, and said bicarbonate is sodium bicarbonate.

20. A composition in accordance with claim 19, wherein said coating comprises a water soluble starch.

21. A composition in accordance with claim 20, wherein said coating is provided on both said sodium bicarbonate and urea peroxide.

22. A composition in accordance with claim 21, further including a foaming agent.

23. A composition in accordance with claim 22, wherein said foaming agent is sodium lauryl sulfate which has been provided with a coating of said water soluble starch.

24. A composition in accordance with claim 22, including from about 1 to 15% by weight of a dentally acceptable abrasive.

25. A composition in accordance with claim 23, including as a dentally acceptable abrasive, from 1 to 50% by weight of calcium diphosphate which has been provided with a coating of said water soluble starch.

26. A composition in accordance with claims 13 or 14, further including a flavoring agent which has been provided with said water soluble barrier coating.

27. A composition in accordance with claim 1 or 13 wherein said water-soluble, non-aqueous vehicle comprises one or more polyalkylene glycols having a molecular weight in the range of about 200 to about 20,000.

* * * * *